United States Patent
Gorman et al.

(10) Patent No.: US 6,451,610 B1
(45) Date of Patent: Sep. 17, 2002

(54) METHOD AND APPARATUS FOR COAGULATION BASED ASSAYS

(75) Inventors: Anne Jessica Gorman, Jamesburg; Robert Samo, Lakewood; John Gorman, Jamesburg, all of NJ (US)

(73) Assignee: International Technidyne Corporation

( * ) Notice: Subject to any disclaimer, the term of this patent is extended or adjusted under 35 U.S.C. 154(b) by 0 days.

(21) Appl. No.: 09/291,776

(22) Filed: Apr. 14, 1999

(51) Int. Cl.$^7$ ............................................. G01N 33/86
(52) U.S. Cl. ..................... 436/69; 436/164; 436/165; 422/58; 422/73; 356/246; 435/13; 73/64.41; 73/64.43; 600/369
(58) Field of Search .......................... 436/63, 69, 164, 436/165; 422/55, 58, 73, 99, 102; 73/64.41, 64.43; 600/369; 435/13; 356/244, 246

(56) References Cited

U.S. PATENT DOCUMENTS

| | | | | |
|---|---|---|---|---|
| 4,756,884 A | * | 7/1988 | Hillman et al. | 422/73 |
| 5,039,617 A | * | 8/1991 | McDonald et al. | 436/69 |
| 5,091,304 A | | 2/1992 | La Duca et al. | 435/13 |
| 5,302,348 A | * | 4/1994 | Cusack et al. | 422/73 |
| 5,372,946 A | | 12/1994 | Cusak et al. | 436/69 |
| 5,504,011 A | | 4/1996 | Gavin et al. | 436/69 |
| 5,506,146 A | * | 4/1996 | Josef | 436/69 |
| 5,534,226 A | | 7/1996 | Gavin et al. | 422/73 |
| 5,591,403 A | | 1/1997 | Gavin et al. | 422/73 |
| 5,731,212 A | | 3/1998 | Gavin et al. | 436/526 |
| 5,800,781 A | * | 9/1998 | Gavin et al. | 422/73 |
| 5,908,786 A | * | 6/1999 | Moreno et al. | 436/69 |

OTHER PUBLICATIONS

K.M. Brinkhous et al. "Newer Approaches To The Study Of Hemophilia & Hemophiloidal States" JAMA, 154, 1954, pp. 481–486.

R.D. Langdell et al. "Effect of Antihemophilic Factor On One Stage Clotting Tests", J. Lab. Clin, Med. 41, 1953, pp. 637–647.

W.H. Bell and H.G. Alton, "A Brain Extract As A Substitute In The Thromboplastic Generation Test", Nature 174, 1954 pp. 880–881.

R.P. Proctor et al.., "The Partial Thromboplastin Time With Kaolin", Am. J. Clin. Path. 36, 1961, pp. 212–219.

O.D. Ratnoff and J.D Crum, "Activation of Hageman Factor by Solutions of Ellagic Acid", J. Lab. Clin. Med. 63, 1964, pp. 359–377.

C. Hougie, Recalcification Time Test And Its Modificatiion (Partial Thromboplastin Time, Activated Partial Thromboplasticn Time and Expanded Thromboplastin Time), Hematology, 3rd Ed. McGraw Hill Book Co. 1983, pp. 1662–1664.

Paul G. Hattersley, MD "Activated Coagulation Time of Whole Blood", JAMA, 1966, pp. 150–154.

Paul G. Hattersley, "Herparin Anticoagulation", Laboratory Hemotology, 1984, pp. 789–818.

* cited by examiner

*Primary Examiner*—Maureen M. Wallenhorst
(74) *Attorney, Agent, or Firm*—Duane Morris LLP; Arthur L. Plevy

(57) ABSTRACT

An activated partial thromboplastin time (APTT) test is described which employs fresh, whole blood that has not been anticoagulated. The method employs a disposable cuvette having specific reagents placed therein. A sample of whole blood is introduced into the cuvette which is drawn into at least one conduit by a pneumatic pump. Initially, the calcium in the sample is chelated at a first reaction site in the conduit, and thereafter is moved through the conduit to a second reaction site where the sample is coagulated by an APTT reagent. After a predetermined incubation time, the sample is moved to a third reaction site where it is recalcified. Clotting time is measured from the time that the sample is recalcified to the time that clot formation is visibly detected.

23 Claims, 2 Drawing Sheets

METHOD AND APPARATUS FOR COAGULATION BASED ASSAYS

BACKGROUND OF THE INVENTION

1. Field of the Invention

The present invention relates to a method for testing liquid samples, wherein the liquid samples are tested within disposable cuvettes. More particularly, the invention relates to blood clotting assays performed using fresh, non-citrated blood and specific reagents placed in a disposable cuvette.

2. Description of Related Art

Blood clotting is a complex process involving three interacting components: blood vessels, blood coagulation factors, and blood platelets. Blood coagulation factors are proteins or glycoproteins which freely circulate within the body. The blood coagulation factors interact in a mechanism commonly referred to as the coagulation cascade. In this proteolytic activation process, inactive coagulation factors are chemically converted to active enzymes. The active enzyme subsequently converts an inactive enzyme precursor or zymogen to an active state resulting in the conversion of prothrombin to thrombin and fibrinogen to fibrin. The activation of zymogens is crucial to the process.

The final step of clot formation is the conversion of plasma soluble fibrinogen to insoluble fibrin as a result of the cleavage of peptide bonds. Cleavage occurs as the result of the proteolytic enzyme thrombin, which is produced from prothrombin. Conversion of prothrombin to thrombin requires a number of proteins called clotting factors, in addition to calcium. The fibrin clot is a crosslinked matrix which entraps the formed elements of the blood thereby sealing off the site of bleeding. Formed elements consist of platelets, white blood cells, and red blood cells.

Platelets are cell fragments having multiple roles in the clotting process. By attaching to the exposed collagen matrix of broken blood vessels and to each other, a primary platelet plug seals off the bleeding site. During the aggregation of platelets, chemical components are released into the plasma which are important in the clotting process. One component is platelet factor 3, which is a phospholipid serving as a necessary cofactor in the coagulation cascade.

There are significant differences in the clotting system of the body, i.e., blood solids including red blood cells, white blood cells, and platelets, and the circulatory coagulation factors proteins associated with the plasma. It is the production and metabolism of the coagulation factors which vary within fairly wide ranges among individuals. Whole blood clotting and plasma clotting have different mechanisms and substances. Plasma lacks many elements present in whole blood, namely, platelets, red blood cells, and white blood cells.

Specific blood clotting assays enable the clinician to determine the integrity of the blood coagulation cascade and the efficacy of therapy. An example of a clotting assay is the Partial Thromboplastin Time (PTT) test. This test was first described in an article entitled "Newer Approaches To The Study Of Hemophilia & Hemiphiloidal States" by K. M. Brinkhous et al., JAMA 154:481–486, 1954, and an article entitled "Effect of Antihemophilic Factor On One Stage Clotting Tests" by R. D. Langdell et al., J. Lab. Clin. Med. 41:637–647, 1953. The principle of the PTT is that citrated platelet poor, i.e, depleted, plasma (PPP) is added to a mixture containing platelet factor 3 (PF3) substitute and calcium. The substitute is a phospholipid derived from brain and lung tissue, and is described in an article entitled "A Brain Extract As A Substitute In The Thromboplastin Generation Test" by W. H. Bell and H. G. Alton, Nature 174:880–881, 1954. The PF3 substitute takes the place of platelets in the clotting process. Calcium is required as a necessary component for clotting since the calcium normally present in circulating blood is rendered unusable by the addition of citrate.

The PTT assay is a valuable clinical test, but a relative lack of reproducibility among different individuals makes it difficult to establish a range of normal values. Much of the variability has been attributed to the processes involved in the initial activation of the coagulation cascade. This "contact activation" sequence was found to be highly variable among individuals. By standardizing the rate at which the activation occurs, the reliability of the PTT assay was greatly improved.

Standardization is accomplished by adding an activator to the PTT mixture. Conducting the PTT in the presence of an activator was first described by Proctor and Rapaport in an article entitled "The Partial Thromboplastin Time With Kaolin" by R. P. Proctor et al., Am J. Clin. Path. 36:212–219, 1961. Known as the Activated Partial Thromboplastin Time (APTT) test, the particulate activator kaolin was first used, and later studies demonstrated the use of a soluble plasma activator, ellagic acid. See the article entitled "Activation of Hageman Factor by Solutions of Ellagic Acid" by O. D. Ratnoff and J. D. Crum, J.Lab.Clin.Med. 63:359–377, 1964. The APTT assays presently used in the clinical laboratory are minor modifications of the earlier tests. See the chapter, "Recalcification Time Test And Its Modification (Partial Thromboplastin Time, Activated Partial Thromboplastin Time And Expanded Partial Thromboplastin Time)" by C. Hougie, in the text: Hematology, 3rd edition, ed. Williams, McGraw Hill Book Co., N.Y., ppg. 1662–1664, 1983.

By eliminating the variable nature of activation, the APTT test is more reliable than PTT. It is particularly useful in identification of clotting factor deficiencies, of which the most common are the Hemophilias: Hemophilia A (Factor VIII deficiency), Hemophilia B (Factor XI deficiency), and Hemophilia C (Factor XII deficiency). It is also valuable as a means to monitor the effect of clot inhibiting agents such as heparin, an animal derived substance which interferes with the formation of the fibrin clot.

The APTT test is generally performed with citrated platelet poor plasma, and employs two active ingredients, a contact activator consisting of kaolin or ellagic acid, and a source of phospholipids. Other contact activators include celite, glass beads, and colloidal silica. Sources of phospholipids include, for example, phosphatidyl choline, phosphatidyl serine, ethanolamine, and other neutral lipids. The blood sample is obtained by hospital personnel and transported to a central laboratory for testing. Plasma is obtained from citrated whole blood. The plasma is placed in a reaction vessel to which the APTT reagents and calcium are added. The sample is incubated for three to five minutes at 37° C. with an equal volume of liquid APTT reagent to allow full activation of Factors XI and XII. The phospholipid allows the remaining factors in the intrinsic pathway (prothrombin complex factors) to activate in the presence of calcium. In the absence of calcium, the pathway is blocked and the activated Factors XI and XII accumulate. Thereafter, the mixture is recalcified to activate the prothrombin complex factors and to determine the clotting time. Under these reaction conditions, a normal APTT clotting time would be in the range of twenty-five to forty seconds, depending upon the reagent, the instrument, and the patient being tested. The two step process is necessary as the APTT test requires a period of contact activation, which generally ranges from about two to five minutes.

This type of processing has proven economical and practical in screening large numbers of patient plasmas. Although practical in the previous example, the present APTT test is unacceptable in many clinical settings where delay in time between drawing the blood sample and obtaining the APTT result is critical. In response to this problem, a more practical test used is the Activated Clotting Time Test (ACT) (Hattersley, JAMA 196:150–154, 1966). Unlike the APTT, the ACT is performed at the bedside of the patient using non-anticoagulated (non-citrated) blood.

The difference between the ACT and the APTT test is that clot formation proceeds in the ACT test in whole blood in the presence of an activator. Scientists have advocated that such an analysis using whole blood is more indicative of the true coagulation state than inducing clot formation in plasma. Consequently, the APTT test using whole blood has been proposed as a more accurate measure of the coagulant state than the ACT test (P. Hattersley, Heparin Anticoagulation, in the test Laboratory Hemotology, ed. by J. Koepke, Churchill, Livingston, p. 789–818, 1984).

Many devices have been made that are capable of performing a coagulation time test, especially in a laboratory environment. Few of the devices are portable and simple enough to operate by a patient in the home. One of the most difficult aspects of using these devices is the taking of a blood sample from the patient, and the administration of the blood sample to the testing equipment before the natural blood clotting mechanism begins.

Many of the devices and methods for measuring the coagulation time of blood samples are assigned to the assignee herein. For example, U.S. Pat. No. 5,372,946 to Cusak et al., entitled BLOOD COAGULATION TIME TEST APPARATUS AND METHOD, issued on Dec. 13, 1994; relates to a disposable cuvette for retaining a sample of blood and an automated test apparatus and method for analyzing the sample of blood within the cuvette to determine a coagulation time for the sample of blood. The blood is deposited in a fluid reservoir of the cuvette. Within the cuvette is a capillary conduit with at least one restricted region. The blood is caused to traverse the restricted region and a testing machine measures the coagulation time.

Methods of performing blood coagulation tests can be implemented using the device described in the following U.S. patents to Gavin et al. and assigned to the assignee herein: U.S. Pat. No. 5,731,212 entitled TEST APPARATUS AND METHOD FOR TESTING CUVETTE ACCOMMODATED SAMPLES, issued on Mar. 24, 1998; U.S. Pat. No. 5,591,403, entitled PORTABLE PROTHROMBIN TIME TEST APPARATUS AND ASSOCIATED METHOD OF PERFORMING A PROTHROMBIN TIME TEST, issued on Jan. 7, 1997; which is a division of U.S. Pat. No. 5,534,226, entitled PORTABLE TEST APPARATUS AND ASSOCIATED METHOD OF PERFORMING A BLOOD COAGULATION TEST, issued on Jul. 9, 1996; which is a division of U.S. Pat. No. 5,504,011, entitled PORTABLE TEST APPARATUS AND ASSOCIATED METHOD OF PERFORMING A BLOOD COAGULATION TEST, issued on Apr. 2, 1996; the disclosures of which are incorporated herein by reference. The portable test apparatus includes a disposable cuvette with multiple conduits. Each of the conduits contains a dried or lyophilized activation reagent. The blood in each of the conduits is reciprocally moved across a restricted region until a predetermined degree of coagulation occurs.

An APTT test is described in U.S. Pat. No. 5,091,304 to La Duca, entitled WHOLE BLOOD ACTIVATED PARTIAL THROMBOPLASTIN TIME TEST AND ASSOCIATED APPARATUS, issued on Feb. 25, 1992; assigned to the assignee herein, where the citrate anticoagulant step is simultaneously combined with the contact activation step to allow one to employ fresh, whole blood specimens. The specific combination in a test tube of reagents which are lyophilized or in liquid form include citrate, activator, and phospholipid. Freshly drawn blood is added to the test tube, which is agitated and heated for three minutes. Calcium is then added to initiate clotting. The blood is inspected every 3–5 seconds until clot formation is observed. Upon formation of a sufficient clot, the blood fails to move freely within the test tube upon tilting.

The present methods of determining clotting time provide clotting times of 70 to 90 seconds, depending upon the patient being tested, and only loosely correlate to any given laboratory test employing plasma in an APTT test. The inability to duplicate the hemostatic status of the patient is a problem when employing whole blood in these laboratory assays.

There remains a need for a method of performing a coagulation-based assay employing whole blood which does not need to be citrated prior to performing the assay which avoids inconvenience to the patient while providing accurate results when screening for clotting abnormalities. The APTT times obtained from the present method are substantially close to those obtained in a clinical laboratory which employs citrated whole blood to obtain normal donor clotting times of 25–35 seconds.

SUMMARY OF THE INVENTION

Briefly described, the invention comprises a method of performing a coagulation-based assay on a fresh whole blood sample. A cuvette having at least one conduit has at least one restriction disposed between the first and second ends of the conduit. After drawing a sample of blood from a patient, a predetermined volume of the blood sample is introduced into the first end of the conduit. At a first position in the conduit is an anticoagulating agent capable of mixing with the blood sample. At a second position in the conduit is a coagulation reagent capable of mixing with the blood sample. At a third position located between said at least one restriction and the second end of the conduit is a recalcification agent.

The whole blood sample is mixed by pneumatic pumping at the first position for a predetermined period of time after which the blood sample is moved to the second position, where it incubates with the coagulation reagent, or APTT reagent for a predetermined period of time at a predetermined temperature. After mixing the sample with the coagulation reagent for approximately three to five minutes, the sample is moved to the third position in the conduit. At the third position, the sample is recalcified. The time until clot formation is measured by visual detection after pulling the sample through the restriction to the third position where it contacts a calcium agent.

Suitable anticoagulating reagents or calcium chelating agents which chelate the free calcium ions present in the blood include citrates, aminocarboxylates such as EDTA, oxalates, and heparin, and the like, as discussed in e.g. "Diagnostic Hematology" by Lawrence Powers, Chapter 25, pages 417 to 420. In a preferred embodiment, a citrate salt is used. Suitable APTT reagents include diatomaceous earth, sodium citrate, phospholipid, and a barbital buffered saline, comprising sodium barbital, sodium chloride, sodium azide, and bovine albumen, and the like, as described in U.S. Pat. No. 5,091,304 to La Duca, the disclosure of which is incorporated herein by reference. Other APTT reagents are known, and any suitable coagulation reagent may be employed. Suitable coagulation reagents include APTT, ACT, prothrombin time, or snake venom reagents (e.g. Russel's viper venom), and the like, depending upon the assay to be performed. The recalcification reagent includes calcium in the form of a salt, such as calcium chloride, calcium gluconate, calcium glycine, and calcium imidodiacetate, and the like. Suitable stabilizers, surfactants, fillers and buffers can optionally be added to the recalcification reagent. Suitable surfactants include Pluronic L18, F68, and the like. Suitable fillers include Trehalose, M700, and the like. Suitable buffers include Hepes buffer having a pH of about 7.4 and a concentration of about 0.02M.

The method of the present invention is used to monitor the integrity of the intrinsic pathway of blood coagulation. In the present invention, calcium is always present, that is, there is no need to citrate or chelate the calcium present in whole blood prior to placing it in the cuvette.

BRIEF DESCRIPTION OF THE DRAWINGS

The above and other features and aspects of the present invention will become more apparent upon reading the following detailed description in conjunction with the accompanying drawings, in which.

DETAILED DESCRIPTION OF THE INVENTION

During the course of this description, like numbers will be used to identify like elements according to the different views which illustrate the invention.

Although the present invention can be used in many different applications, the present invention is particularly suitable for use in testing whole blood samples. Accordingly, the present invention will be described in connection with testing of whole blood samples to provide an exemplary embodiment of the method. The cuvette employed is a modified version of the cuvette described in detail in U.S. Pat. No. 5,731,212 to Gavin et al., and assigned to the assignee herein, the disclosure of which is incorporated herein by reference.

Figure 1:
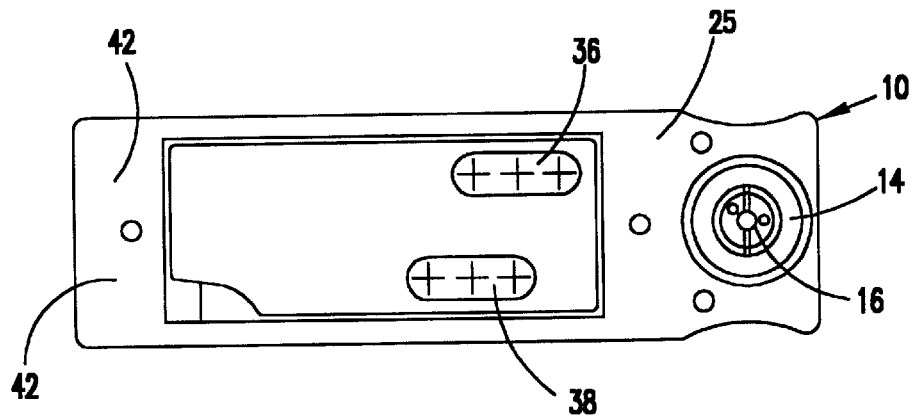
FIG. 1 is a top view of the cuvette employed in the method of the invention.
Figure 2:
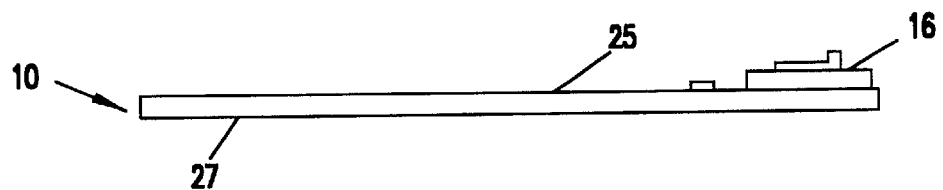
FIG. 2 is a side view of the cuvette employed in the method of the invention.
Figure 3:
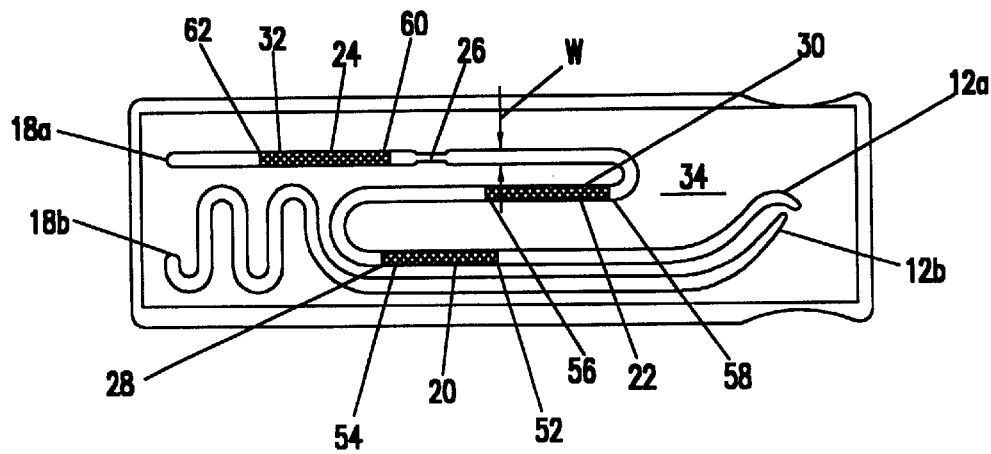
FIG. 3 is a bottom view of the cuvette employed in the method of the invention.

Referring to FIG. 1 in conjunction with FIG. 2 and FIG. 3, a cuvette 10 employed in the method of the invention is shown. As shown in FIG. 1, the top surface 25 of the cuvette has a common supply area 14 having an aperture 16 through which test fluid is introduced into the cuvette. Also shown in FIG. 1 is a series of LEDs 36 and 38 which allow one to check the volume of the sample at various stages of the process.

Referring to FIG. 2, a side view of the cuvette 10 is shown. The cuvette 10 is formed as a unitary device. The top view of FIG. 1 and the bottom view of FIG. 3 show the features of the unitary molded cuvette 10 unitary device of FIG. 2. Conduits 12a and 12b are formed in the bottom surface 27 of the cuvette 10 shown in FIG. 2. Common supply area 14 and aperture 16 are formed in the top surface 25 of the cuvette 10, the aperture 16 of which extends through the bottom surface 27.

Figure 4:
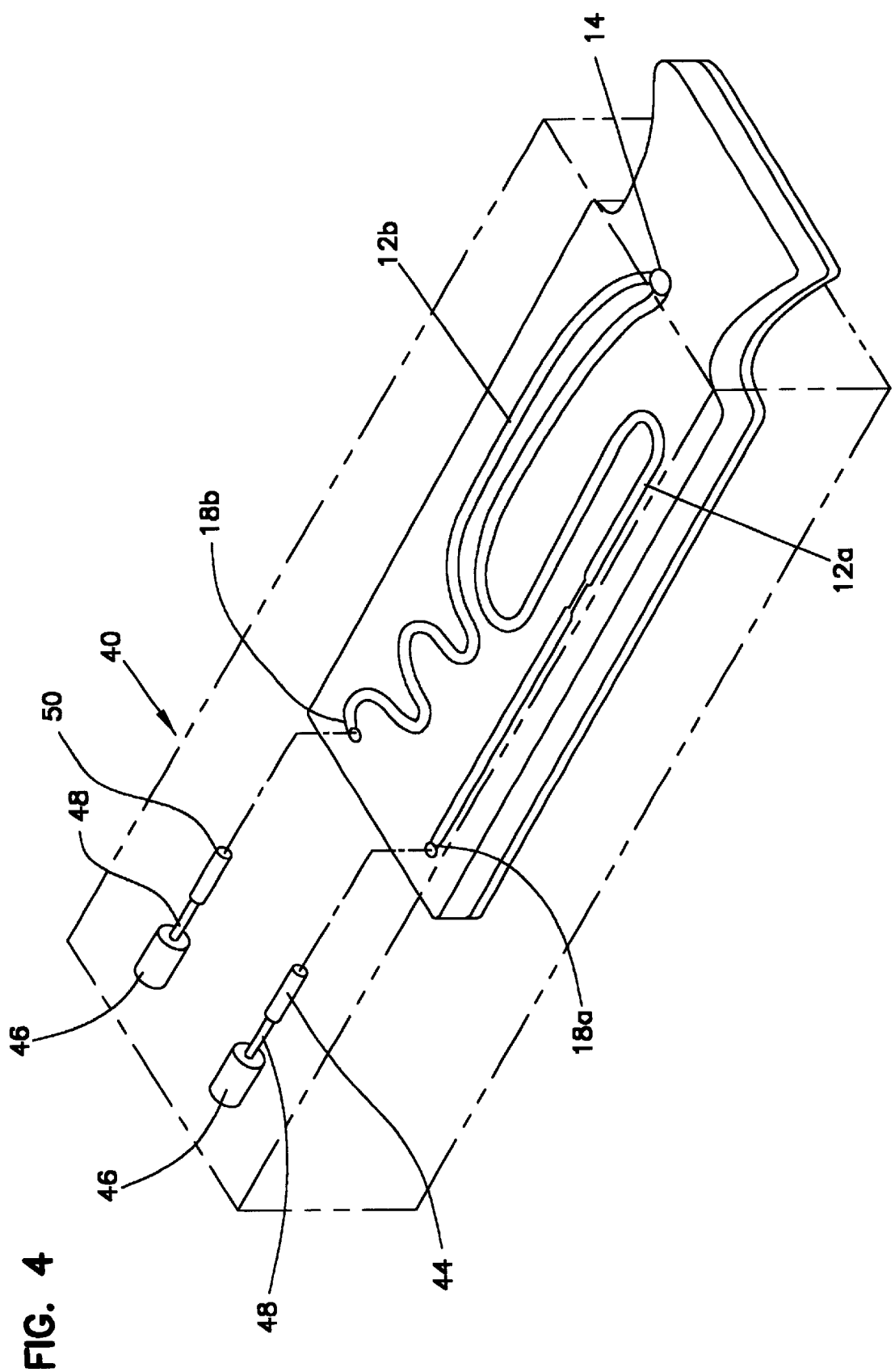
FIG. 4 is a perspective, fragmented view of the cuvette of FIGS. 1–3 shown in conjunction with a schematic representation of a test apparatus.

The cuvette 10 is preferably made of a transparent material for ease in visually detecting clot formation, and which does not react with the selected reagents placed therein. As shown in FIG. 3, two conduits 12a and 12b are defined within the cuvette 10. Although two conduits are shown, the cuvette defines at least one conduit 12a or a plurality of conduits as desired, depending upon the test to be performed. In the embodiment shown, conduit 12b is used as a drain channel. The opposite ends 18a and 18b of each of the conduits 12a and 12b terminate at pumping ports 42 which extend through the top surface 25 of the cuvette 10 to the ends 18a and 18b of the conduit as seen in FIG. 4.

Although each of the conduits can be sized differently, each conduit in the cuvette 10 should have a height H and a width W (FIG. 3) which is large enough to prevent a significant amount of capillary flow within the conduits. Since capillary action provides only one-way flow, the sample to be tested is prevented from being moved reciprocally within the cuvette 10. Capillary action also prevents the temporary pausing of the sample in a position for testing prior to advancing to a second position.

Referring to FIG. 3, at a first location 20 in the cuvette 10, an anticoagulating reagent 28 is placed within the conduit 12a. At a second location 22 in the cuvette, a coagulating reagent 30 is likewise placed therein. At a third location 24, the calcium reagent 32 is placed in the conduit 12a. Between the second location 22 and the third location 24 at least one restrictive area 26 within the conduit 12a is formed. As can be seen, the cuvette 10 differs from that described in the Gavin patents previously discussed. Between each reaction site, the conduit 12a curves in essentially a half-circle formation. It is this configuration that allows all three reagents to be placed in a single cuvette 10 to implement the method of the present invention. The configuration of the cuvette 10 also avoids the need to provide a restriction between each reaction site in order to mix the reagents with the sample. As will be discussed, the mixing is controlled by a pneumatic pump and by microprocessor controls.

The reagent compounds are deposited as liquid slugs into the various positions within the conduit 12a as the cuvette is manufactured. There should be no particles or foreign material inside the conduits 12a and 12b and the restrictive area 26 prior to adding the specific reagents. In the preferred embodiment, the reagent compounds 28, 30, and 32 are air-dried for at least two hours. After the liquid slugs are air-dried, a clear, transparent adhesive tape 34 is placed on the bottom of the cuvette 10 to maintain the sample when it is placed within the cuvette 10. The tape 34 should be pressed firmly so there are no bubbles, folds, or other similar imperfections on the bottom surface 27 of the cuvette 10. The tape 34 should thus be smoothly bonded to the bottom surface 27 of the cuvette 10. Although the cuvette 10 shown has three reaction sites, the number of sites can be increased or decreased, as desired.

The reagent formulations employed in the method must be optimized for performance. Thus the reagents must be capable of air drying and remaining stable upon drying to provide optimal coagulation activity of the dried reagent. The reagent selected must also be easily placed in the conduit of the cuvette while providing the optimal amount of reagent for reproducible clotting times.

Referring to FIG. 4, when the cuvette 10 is placed within a test machine 40, pneumatic pumps 44 couple to the pumping ports 42 on the top surface 25 of the cuvette 10. Operation of the pumps 44 is described in U.S. Pat. No. 5,591,403 to Gavin et al. As a result, the space within each of the conduits 12a and 12b is pneumatically coupled to a pump capable of either increasing or decreasing the air pressure within the confines of the conduits. In the shown embodiment, the pneumatic pumps 44 are positive displacement pumps that work by the use of a stepper motor 46 that drives a piston 48 back and forth within a pumping chamber 50. By advancing the piston 48 within the pumping chamber 50, air pressure within the conduits can be raised above ambient pressure. When retracting the piston 48 within the chamber 50, air pressure within the conduits can be reduced below ambient pressure. In the embodiment shown, there are two pneumatic pumps, one controlling the sample conduit 12a and one controlling the waste conduit 12b. The length of time required to form a clot is measured using a suitable whole blood analyzer, for example, the Hemochron, Jr., available from the assignee herein. The length of time required for the clot to form is related to the integrity of the clotting cascade.

The pneumatic pumps 44 have a microprocessor control, similar to that described in U.S. Pat. No. 5,372,946 to Cusak et al, entitled BLOOD COAGULATION TIME TEST APPARATUS AND METHOD, a division of U.S. Pat. No. 5,302,348, issued on Apr. 12, 1994, assigned to the assignee herein, the disclosure of which is incorporated herein by reference. To begin the coagulation time test on the whole blood sample, the pneumatic pump draws a predetermined volume of blood into the test conduit 12a from the common supply area 14. The pneumatic pump is then cycled causing the blood within the test conduit 12a to reciprocally move back and forth in the respective reaction sites. As the blood sample is cycled back and forth, sensors are used to control the time that elapses, which is predetermined depending upon the size of the sample. After the blood is drawn into the conduit 12a, residual blood from the common supply area 14 is drawn into the drain conduit 12b. Thus, no open reservoirs of blood remain when the cuvette is removed from the testing machine.

After a blood sample is placed in the aperture 16 of the common supply area 14, the sample passes through a series of light emitting diodes (LEDs) where the volume of the sample is checked. Fresh, whole blood is drawn into the cuvette 10 along the conduit 12a by the pump 44 where it rehydrates and is mixed with the reagent located at the first position 20 in the conduit 12a. In the preferred embodiment, the blood sample is anticoagulated in the first position 20 by mixing the sample with a predetermined amount of a suitable anticoagulant such as a citrate salt, preferably trisodium citrate or potassium citrate, to prevent the blood sample from clotting. Other preferred embodiments include citrate compounds such as sodium citrate, citrate dextrose, citrate phosphate dextrose, and citric acid, and the like. While the amount of citrate employed depends upon the size of the conduit, and the amount of the sample to be tested, generally an amount in the range of 5–10 $\mu$l is sufficient to citrate the whole blood sample, provided that the concentration is greater than the normal concentration of calcium ions typically found in human blood. The sample is then mixed for a predetermined period of time by advancing and retracting the pumps 44 between locations 52 and 54. To ensure complete mixing of the reagent with the sample, mixing should take place for at least 30 seconds.

Thereafter, the anticoagulated sample is moved by at least one of the pumps 44 to the second position 22 within the conduit 12a. The anticoagulated sample is then mixed with a predetermined amount of suitable coagulating reagent, the selection of which depends upon the clotting factor deficiencies to be identified. For example, any known prothrombin time reagent preparation may be employed to test for Factors II, VII and X; any suitable snake venom such as Russel's Viper Venom, which tests for Factor X; and any suitable APTT preparation, such as Dade Actin FSL, available from Dade International, Inc. of Deerfield, Ill., to test for Factors VIII, IX, XI and XII. A suitable prothrombin time reagent includes human or animal brain extract or recombinant tissue factor in the preparation, also available from Dade International, Inc. Dade Actin FSL is a mixture of several activator reagents and a phospholipid, and is factor sensitive to lupus. While the amount of coagulating reagent employed depends upon the size of the conduit, and the amount of sample to be tested, generally an amount in the range of 5–10 $\mu$l is sufficient for mixing with the citrated whole blood sample. The sample is then mixed for a predetermined period of time at the second reaction site 22 by advancing and retracting the pumps 44 between locations 56 and 58. To ensure complete mixing of the reagent with the citrated sample, mixing should take place for at least 30 seconds. For the APTT test, mixing should take about three to five minutes, to allow full activation of the contact (FXI and FXII) factors. The mixing can be controlled in thirty second increments to obtain optimal results, since the mixing time varies depending upon the reagent selected for use in the assay. Prior to moving the sample through the restrictive area 26, the sample passes through a series of LEDs where the volume of the sample is checked.

After the sample is moved through the restrictive area 26 of the conduit 12a to the third position 24 in the conduit 12a, it is mixed with a predetermined amount of calcium reagent 32 between locations 60 and 62 to initiate the clotting mechanism. While the amount of calcium reagent employed depends upon the size of the conduit and the amount of the sample to be tested, generally an amount in the range of 5–10 $\mu$l is sufficient to initiate the mechanism. In the preferred embodiment, a suitable source of calcium is calcium chloride, calcium gluconate, calcium glycine, and calcium imidodiacetate. Thus, the clotting mechanism is reinitiated by adding calcium ions to the sample, in an amount sufficient to have free calcium (i.e. non-chelated calcium) in the sample. From the time that the sample passes through the restrictive area 26 of the conduit 12a and contacts the calcium reagent, the clotting time is measured until the restrictive area 26 becomes blocked by detectable clot formation. Blockage in the restrictive area is easily determined visually as the cuvette is transparent.

The APTT times obtained from the present method are substantially close to those obtained in a clinical laboratory or fibrometer which employs citrated whole blood to obtain normal donor values. By performing all three steps in the cuvette in sequence, the problems associated with performing the test with previously citrated platelet-poor plasma are avoided.

The length of time required for the clot to form is related to the integrity of the coagulation cascade. Patient results with longer clotting times than the pre-established normal range are indicative of a coagulation factor deficiency or the presence of an anticoagulant, such as heparin. By monitoring the results of the APTT test, the clinician may properly ascertain the integrity of the clotting system, diagnose deficient states, or the presence of anticoagulants.

In an alternate embodiment of the method of the invention, the cuvette 10 can be used for immunodiagnostics. Whole blood freshly drawn from a patient is tested for a targeted antigen by mixing with selected reagents. Measurement of practically any analyte can be made using the following technique. At the first reaction site 20, a soluble labeled antibody is mixed with the sample to react with the antigen of interest. The reagent compound includes magnetic particles joined to the labeled antibody. A solid phase capture antigen is placed at the second reaction site 22 to pick up any unreacted antibody. At the third reaction site 24, an enzyme substrate reacts with the enzyme labeled antibody. Colorimetric detection is performed for the targeted antigen. If detection of fluorescent labeled antibodies after binding with antigens is desired, no third reaction is required. Examples of suitable analytes include Prothrombin Fragment 1.2, soluble fibrin, tPA, and Hirulog.

While the invention has been described with reference to the preferred embodiment thereof, it will be appreciated by those of ordinary skill in the art that modifications can be made to the parts that comprise the invention without departing from the spirit and scope thereof. The following example will serve to further typify the nature of the invention but should not be construed as a limitation on the scope thereof, which is defined solely by the appended claims.

EXAMPLE 1

A cuvette is filled with 10 μl of 0.57% (w/v) trisodium citrate at a first reaction site, 10 μl of Dade ACTin FSL at a second reaction site, and 5 μl of 25 mM $CaCl_2$ in a third reaction site. The cuvette is air dried overnight at 20° C. with 5% relative humidity. A thin, transparent adhesive tape is placed over the bottom of the cuvette.

An 18 μl whole blood sample from a patient is placed in the aperture of the common supply area of the cuvette. The sample is drawn to the first reaction site where it is citrated with the anticoagulating reagent by mixing for about thirty seconds at a rate of approximately 40 pump steps per second. Thereafter, the calcium chelated sample is moved to the second reaction site where it is mixed for three minutes to allow activation of Factors FXI and FXII. After three minutes of incubation, the sample is pulled through the restriction in the conduit, where it contacts the calcium. From the point of contact with the recalcification reagent, the clotting time is measured until the first sign of fibrin formation is visible through the cuvette. Normal clotting times between 25 and 35 seconds are thus obtained.

What is claimed is:

1. A method of performing a coagulation-based assay on a fresh whole blood sample, comprising the steps of:
   providing a cuvette having at least one substantially non-capillary conduit having a first end and a second end, said at least one conduit having a restriction disposed between said first end and said second end of said conduit;
   introducing a predetermined volume of said blood sample into said first end of said at least one conduit;
   providing an anticoagulating agent at a first position in said at least one conduit, wherein said anticoagulating agent is capable of mixing with said blood sample;
   providing a coagulation agent in a second position in said at least one conduit, a portion of said conduit between said first position and said second position curving in a half-circle formation, wherein said coagulation reagent is capable of mixing with said blood sample;
   providing a recalcification agent at a third position in said at least one conduit, said third position located between said restriction and said second end of said at least one conduit, wherein said recalcification agent is capable of mixing with said blood sample;
   moving said blood sample from said first position to said second position, and from said second position to said third position; and
   measuring the time it takes for said blood sample to clot.

2. The method according to claim 1, wherein the anticoagulating agent is selected from the group consisting of citrates, amino carboxylates, oxalates and heparin.

3. The method according to claim 2, wherein the anticoagulating agent comprises a citrate.

4. The method according to claim 3, wherein the anticoagulating agent is selected from the group consisting of sodium citrate, trisodium citrate, and potassium citrate.

5. The method according claim 1, wherein the coagulation agent is selected from the group consisting of diatomaceous earth, kaolin, ellagic acid, silica, celite, phospholipids, and mixtures thereof.

6. The method of claim 1, wherein the recalcification agent is selected from the group consisting of calcium chloride, calcium gluconate, calcium glycine, and calcium imidodiacetate.

7. The method according to claim 1, wherein said blood sample is moved by pneumatic pumping.

8. A method of performing a coagulation-based assay on a fresh whole blood sample, comprising the steps of:
   providing a cuvette having at least one substantially non-capillary conduit, said at least one conduit having a first end and a second end, wherein at least one restriction is disposed between said first end and said second end of said conduit;
   introducing a predetermined volume of said blood sample into said first end of said at least one conduit;
   providing a calcium chelating agent at a first position in said at least one conduit in a predetermined amount, wherein said calcium chelating agent mixes with said blood sample for a predetermined period of time;
   moving said calcium chelated blood sample along said at least one conduit to a second position, a portion of said conduit between said first position and said second position curving in a half-circle formation;
   providing a coagulation agent at said second position in said at least one conduit in a predetermined amount, wherein said coagulation agent mixes with said calcium chelated blood sample for a predetermined period of time;
   moving said coagulated blood sample along said at least one conduit to a third position;
   providing a recalcification agent at said third position in said at least one conduit in a predetermined amount, said third position located between said at least one restriction and said second end of said at least one conduit, wherein said coagulated blood sample contacts said recalcification agent; and
   measuring the time it takes for said blood sample to clot.

9. The method according to claim 8, wherein the calcium chelating agent is selected from the group consisting of citrates, amino carboxylates, oxalates, and heparin.

10. The method according to claim 8, wherein the calcium chelating agent comprises a citrate.

11. The method according to claim 10, wherein the calcium chelating agent is selected from the group consisting of sodium citrate, trisodium citrate, and potassium citrate.

12. The method according to claim 8, wherein the coagulation agent is selected from the group consisting of diatomaceous earth kaolin, ellagic acid, silica, celite, phospholipids, and mixtures thereof.

13. The method according to claim 8, wherein the recalcification agent is selected from the group consisting of calcium chloride, calcium gluconate, calcium glycine, and calcium imidodiacetate.

14. The method according to claim 8, wherein said blood sample is moved by pneumatic pumping.

15. The method according to claim 8, wherein said predetermined period of time wherein said calcium chelating agent mixes with said blood sample is about 30 seconds.

16. The method according to claim 8, wherein said predetermined period of time wherein said coagulation agent mixes with said calcium chelated blood sample ranges from about three to five minutes.

17. A method of performing an activated partial thromboplastin time test on a fresh whole blood sample, comprising the steps of:

providing a cuvette having at least one substantially non-capillary conduit having a first end and a second end, wherein at least one restriction is disposed between said first end and said second end of said at least one conduit;

introducing a predetermined volume of said blood sample into said first end of said at least one conduit of said cuvette;

providing an anticoagulating agent at a first position in said at least one conduit, wherein said anticoagulating agent mixes with said blood sample for a predetermined period of time to chelate calcium present in said blood sample;

moving said anticoagulated blood sample along said at least one conduit to a second position, a portion of said conduit between said first position and said second position curving in a half-circle formation;

providing a coagulation agent at said second position in said at least one conduit, wherein said coagulation agent mixes with said anticoagulated blood sample for a predetermined period of time to allow activation of deficiency factors and coagulation of said blood sample;

providing a recalcification agent at a third position in said at least one conduit, said third position located between said at least one restriction and said second end of said at least one conduit;

moving said coagulated blood sample through said at least one restriction to said third position, wherein said coagulated blood sample contacts and is recalcified by said recalcification agent; and measuring the time it takes for said blood sample to clot from the time the coagulated blood sample contacts said recalcification agent to the time that said at least one restriction in said cuvette is blocked by a clot formation.

18. The method according to claim 17, wherein the anticoagulating agent is selected from the group consisting of citrates, amino carboxylates, oxalates, and heparin.

19. The method according to claim 18, wherein the anticoagulating agent comprises a citrate salt.

20. The method according to claim 19, wherein the anticoagulating agent is selected from the group consisting of sodium citrate, trisodium citrate, and potassium citrate.

21. The method according to claim 11, wherein the coagulation agent is selected from the group, consisting of diatomaceous earth, kaolin, ellagic acid, silica, celite, phospholipids, and mixtures thereof.

22. The method according to claim 17, wherein the recalcification agent is selected from the group consisting of calcium chloride, calcium gluconate, calcium glycine, and calcium imidodiacetate.

23. The method according to claim 17, wherein said blood sample is moved by pneumatic pumping.

* * * * *